US006239128B1

United States Patent
Watjen et al.

(10) Patent No.: US 6,239,128 B1
(45) Date of Patent: May 29, 2001

(54) INDOLE-2,3-DIONE-3-OXIME DERIVATIVES FOR THERAPEUTIC USE

(75) Inventors: Frank Watjen; Jorgen Drejer, both of Ballerup (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 09/675,214

(22) Filed: Sep. 29, 2000

Related U.S. Application Data

(63) Continuation of application No. PCT/DK99/00194, filed on Mar. 30, 1999.

(30) Foreign Application Priority Data

Mar. 31, 1998 (DK) .................................... 0452/98
Apr. 1, 1998 (DK) .................................... 0462/98

(51) Int. Cl.⁷ ........................... A61K 31/55; A61K 31/44; A61K 31/40
(52) U.S. Cl. ........................... 514/217; 514/291; 514/411
(58) Field of Search .................................... 514/217, 291, 514/411

(56) References Cited

FOREIGN PATENT DOCUMENTS

A19426747   11/1994   (WO).
A19814447   9/1998    (WO).

*Primary Examiner*—Raymond Henley, III
(74) *Attorney, Agent, or Firm*—Birch, Stewart, Kolasch & Birch, LLP

(57) ABSTRACT

The present invention relates to the use of indole-2,3-dione-3-oxime derivatives in a method of combating diseases and disorders associated with or mediated by the release of excitatory amino acids.

10 Claims, No Drawings

INDOLE-2,3-DIONE-3-OXIME DERIVATIVES FOR THERAPEUTIC USE

This application is a Continuation of PCT International Application No. PCT/DK99/00194 filed on Mar. 30, 1999, which designated the United States and on which priority is claimed under 35 U.S.C. §120, the entire contents of which are hereby incorporated by reference.

TECHNICAL FIELD

The present invention relates to the use of indole-2,3-dione-3-oxime derivatives in a method of combating diseases and disorders associated with or mediated by the release of excitatory amino acids.

BACKGROUND ART

Excessive excitation by neurotransmitters can cause the degeneration and death of neurones. It is believed that this degeneration is in part mediated by the excitotoxic actions of the excitatory amino acids (EAA), glutamate and aspartate, at the N-methyl-D-aspartate (NMDA), the alfa-amino-3-hydroxy-5-methyl-4-isoxazole propionic acid (AMPA) receptor, and the kainate receptor. This excitotoxic action is responsible for the loss of neurones in cerebrovascular disorders such as cerebral ischemia or cerebral infarction resulting from a range of conditions, such as thromboembolic or haemorrhagic stroke, cerebral vasospasm, hypoglycaemia, cardiac arrest, status epilepticus, perinatal asphyxia, anoxia such as from near-drowning, pulmonary surgery and cerebral trauma as well as lathyrism, Alzheimer's, and Huntington's diseases. Compounds capable of blocking excitatory amino acid receptors are therefore considered useful for the treatment of the above disorders and diseases, as well as Amyotrophic Lateral Sclerosis (ALS), schizophrenia, Parkinsonism, epilepsy, anxiety, pain and drug addiction.

DETAILED DISCLOSURE OF THE INVENTION

It has now been found that certain indole-2,3-dione-3-oxime derivatives and pharmaceutically acceptable salts hereof have valuable therapeutic properties.

Thus, viewed from one aspect, the present invention provides a method of combating diseases and disorders associated with or mediated by the release of excitatory amino acids, said method comprising administering to a subject a compound of the general formula (I):

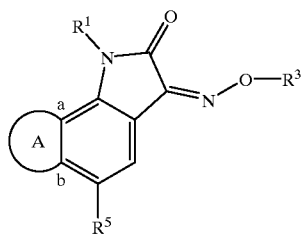

wherein
$R^1$ represents hydrogen, alkyl or benzyl;
$R^3$ represents "Het", or a group of the following formula

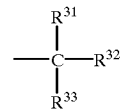

wherein
"Het" represents a saturated or unsaturated, 4 to 7 membered, monocyclic, heterocyclic ring, which ring may optionally be substituted one or more times with substituents selected from the group consisting of halogen, alkyl, alkoxy, and oxo; and
at least one of $R^{31}$, $R^{32}$, and $R^{33}$ independently represents hydrogen, alkyl, or hydroxyalkyl, and
at least one of $R^{31}$, $R^{32}$, and $R^{33}$ independently represents $(CH_2)_n R^{34}$;
wherein
$R^{34}$ represents hydroxy, carboxy, alkoxycarbonyl, alkenyloxycarbonyl, alkynyloxycarbonyl, cycloalkoxycarbonyl, cycloalkyl-alkoxycarbonyl, aryloxycarbonyl, aralkoxycarbonyl, $CONR^{35}R^{36}$, or "Het"; wherein
$R^{35}$ and $R^{36}$ represents hydrogen, alkyl, alkenyl, alkynyl, hydroxyalkyl, cycloalkyl, aryl, aralkyl, or $(CH_2)_n$—$R^{37}$; wherein
$R^{37}$ represents hydroxy, carboxy, alkoxycarbonyl, alkenyloxycarbonyl, alkynyloxycarbonyl, cycloalkoxy-carbonyl, cycloalkyl-alkoxycarbonyl, aryloxycarbonyl, or aralkoxycarbonyl; or
$R^{35}$ and $R^{36}$ together with the N-atom to which they are attached form a saturated 5- to 6-membered, heterocyclic ring, optionally containing one additional N or O atom; and
"Het" is as defined above; and
n is 0, 1, 2, or 3; and
$R^5$ represents phenyl, naphthyl, thienyl, or pyridyl, all of which may be substituted one or more times with substituents selected from the group consisting of halogen, $CF_3$, $NO_2$, amino, alkyl, alkoxy, phenyl and $SO_2NR^{51}R^{52}$;
wherein
$R^{51}$ and $R^{52}$ each independently represents hydrogen or alkyl; or
$R^{51}$ and $R^{52}$ together with the N-atom to which they are attached form a saturated 4- to 7-membered, monocyclic, heterocyclic ring, optionally containing one additional N or O atom; and
"A" represents a ring of five to seven atoms fused with the benzo ring at the positions marked "a" and "b", and formed by the following bivalent radicals:
a-$NR^6$—$CH_2$—$CH_2$-b;
a-$CH_2$—$NR^6$—$CH_2$-b;
a-$CH_2$—$CH_2$—$NR^6$-b;
a-$NR^6$—$CH_2$—$CH_2$—$CH_2$-b;
a-$CH_2$—$NR^6$—$CH_2$—$CH_2$-b;
a-$CH_2$—$CH_2$—$NR^6$—$CH_2$-b;
a-$CH_2$—$CH_2$—$CH_2$—$NR^6$-b;
a-$NR^6$—$CH_2$—$CH_2$—$CH_2$—$CH_2$-b;
a-$CH_2$—$NR^6$—$CH_2$—$CH_2$—$CH_2$-b;
a-$CH_2$—$CH_2$—$NR^6$—$CH_2$—$CH_2$-b;
a-$CH_2$—$CH_2$—$CH_2$—$NR^6$—$CH_2$-b; or a-$CH_2$—$CH_2$—$CH_2$—$CH_2$—$NR^6$-b; wherein
$R^6$ represents hydrogen, alkyl or $CH_2CH_2OH$;
or a pharmaceutically acceptable salt thereof.

Diseases included in the method of the invention include in particular diseases of the central nervous system (CNS). In particular, the invention relates to combating diseases associated with reduced blood flow to the brain and other CNS tissue and with instances of a temporary break in blood supply to the brain or to other CNS tissue. Examples include ischaemic diseases, anoxic episodes, and injury to the brain and other parts of the CNS caused by trauma or other injury, for example a blow to the head, or spinal injury. In such reduced blood flow episodes, or episodes where there is a temporary break in blood supply, oxygen supply to the brain is reduced or interrupted. It is believed that this results in a release of neurotransmitters such as glutamate into the area of the brain where there is oxygen deprivation; the binding of the released neurotransmitters to the cellular neurotransmitter receptors triggers various cellular and biochemical events which can lead to cell death. These receptors include the glutamate receptor, the aspartate receptor, the N-methyl-D-aspartate (NMDA) receptor, the alfa-amino-3-hydroxy-5-methyl-4-isoxazole propionic acid (AMPA) receptor and the kainate receptor. It is further believed that the 2,3-dione-3-oxime derivative for use in the invention block these cellular receptors, thereby preventing the catastrophic chain of events including neurone death which can follow the release of neurotransmitters such as glutamate.

The method of the invention may be used in the treatment or prevention of cerebrovascular disorders such as cerebral ischemia or cerebral infarction resulting from a range of conditions, such as tromboembolic or haemorrhagic stroke, cerebral vasospasm, hypoglycaemia, cardiac arrest, status epilepticus, perinatal asphyxia, anoxia such as from near-drowning, pulmonary surgery and cerebral trauma as well as lathyrism, Alzheimer's disease, and Huntington's disease. The method can be used in the treatment or prevention of traumatic brain injury, in particular ischaemic, hypoxic or anoxic brain damage, spinal cord injury, tissue ischemia and reperfusion injury in a mammal at risk for such damage.

The brain damage may follow cerebral ischemia, either global or focal, or be caused by cardiac arrest, or may follow high risk surgery such as cardiac surgery. It may also follow or be caused by stroke, neonatal hypoxia, hypoxia caused by compromised lung function, neonatal anoxia, anoxia caused by compromised lung function, cerebral trauma, secondary regional ischemia induced by brain oedema, increased intercranial pressure, open brain surgery, endarterectomy, surgical interventions involving temporary, artificially sustained arrest of cardiopulmonary functions resulting in impairment of cerebral blood flow, and emergency treatment involving cardiopulmonary resuscitation (CPR).

As used herein, reperfusion injury refers to the cellular changes and tissue damage seen after a period of total ischemia followed by reperfusion. Extremity replantation, organ transplantation, free flap tissue reconstruction and even myocardial infarction and stroke are all clinical examples of interval tissue ischemia which can lead to tissue loss due to reperfusion injury after blood flow is re-established. Tissue reperfusion injury, seen in its full clinical extent as the no-reflow phenomenon, appears as inflammatory response to reperfusion resulting in the ultimate death of the tissue.

Thus the chemical compounds of the invention are found to be particularly useful in acute treatment of ischaemic stroke, in treatment of brain damage following global cerebral ischemia, or for prevention of brain damage following high risk surgery.

In many instances of brain ischemia, treatment is not available to the patient for several, e.g. up to 6 hours, in stroke patients typically 3 to 6 hours, after the ischaemic injury. Such a delay places great demands on any therapeutic regime designed to mitigate ischaemic brain injury. It has been found, however, that the chemical compounds of the invention is surprisingly effective whether administered pre-ischemically or post-ischemically.

When administered post-ischemically it is advisable that the chemical compounds of the invention be administered within one day of the ischaemic insult. Although the neuroprotective agent used in the invention may be administered as late as 14 hours after brain reperfusion, the treatment should preferably be carried out within 12 hours of ischaemic alleviation or reperfusion. Preferably, the treatment should occur within 6 hours of alleviation of ischemia. Yet more preferred is the administration of the chemical compounds used in the invention within 3 hours of alleviation of ischemia As used herein, CNS includes the brain and spinal cord and combating includes both therapy and diagnosis.

Viewed from a related aspect, the invention provides the use of a compound of formula I (as hereinbefore defined) or a pharmaceutically acceptable salt thereof in the manufacture of a medicament for combating diseases and disorders associated with or mediated by the release of excitatory amino acids.

In a preferred embodiment, the indole-2,3-dione-3-oxime derivatives for use in the invention may be described by the general formula I, above, wherein "Het" is a lactone ring of the general formula (VI):

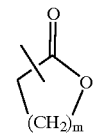

and wherein m is 1, 2, 3 or 4.

In another preferred embodiment, the indole-2,3-dione-3-oxime derivatives for use in the invention may be described by the general formula (II):

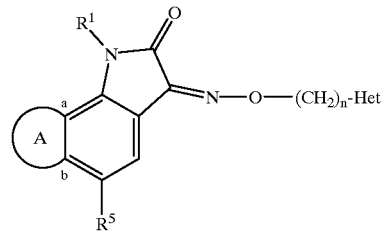

wherein $R^1$ represents hydrogen, alkyl or benzyl;

"Het" represents a saturated or unsaturated, 4 to 7 membered, monocyclic, heterocyclic ring, which ring may optionally be substituted one or more times with substituents selected from the group consisting of halogen, alkyl, alkoxy, and oxo;

n is 0, 1, 2, or 3;

$R^5$ represents phenyl, naphthyl, thienyl, or pyridyl, all of which may be substituted one or more times with substituents selected from the group consisting of halogen, $CF_3$, $NO_2$, amino, alkyl, alkoxy, phenyl and $SO_2NR^{51}R^{52}$;

wherein
$R^{51}$ and $R^{52}$ each independently represents hydrogen or alkyl; or
$R^{51}$ and $R^{52}$ together with the N-atom to which they are attached form a saturated 4- to 7-membered, monocyclic, heterocyclic ring, optionally containing one additional N or O atom; and "A" represents a ring of five to seven atoms fused with the benzo ring at the positions marked "a" and "b", and formed by the following bivalent radicals:
a-$NR^6$—$CH_2$—$CH_2$-b;
a-$CH_2$—$NR^6$—$CH_2$-b;
a-$CH_2$—$CH_2$—$NR^6$-b;
a-$NR^6$—$CH_2$—$CH_2$—$CH_2$-b;
a-$CH_2$—$NR^6$—$CH_2$—$CH_2$-b;
a-$CH_2$—$CH_2$—$NR^6$—$CH_2$-b;
a-$CH_2$—$CH_2$—$CH_2$—$NR^6$-b;
a-$NR^6$—$CH_2$—$CH_2$—$CH_2$—$CH_2$-b;
a-$CH_2$—$NR^6$—$CH_2$—$CH_2$—$CH_2$-b;
a-$CH_2$—$CH_2$—$NR^6$—$CH_2$—$CH_2$-b;
a-$CH_2$—$CH_2$—$CH_2$—$NR^6$—$CH_2$-b; or
a-$CH_2$—$CH_2$—$CH_2$—$CH_2$—$NR^6$-b; wherein
$R^6$ represents hydrogen, alkyl or $CH_2CH_2OH$.

In a more preferred embodiment, the indole-2,3-dione-3-oxime derivatives for use in the invention may be described by the general formula II, above, wherein n is 0, 1 or 2; and $R^5$ represents phenyl or pyridyl, both of which may be substituted one or more times with substituents selected from the group consisting of halogen, $CF_3$, $NO_2$, amino, alkyl, alkoxy, phenyl and $SO_2NR^{51}R^{52}$;

wherein
$R^{51}$ and $R^{52}$ each independently represents hydrogen or alkyl; or
$R^{51}$ and $R^{52}$ together with the N-atom to which they are attached form a chain —$(CH_2)_m$—, wherein m is 2, 3, 4, 5 or 6.

In another preferred embodiment, the indole-2,3-dione-3-oxime derivatives for use in the invention may be described by the general formula (III):

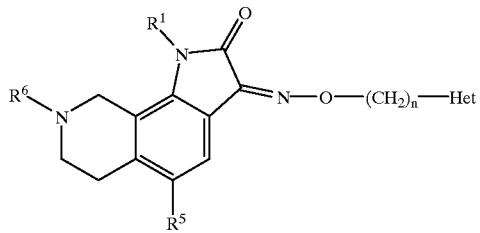

wherein
$R^1$, $R^5$, $R^6$, "Het", and n are as defined above.

In a yet further embodiment, the indole-2,3-dione-3-oxime derivatives for use in the invention may be described by the general formula II, wherein "Het" is a lactone of the general formula (VII):

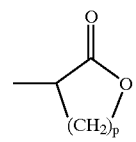

wherein p is 1, 2, 3, or 4.

In another preferred embodiment, the indole-2,3-dione-3-oxime derivatives for use in the invention may be described by the general formula (IV):

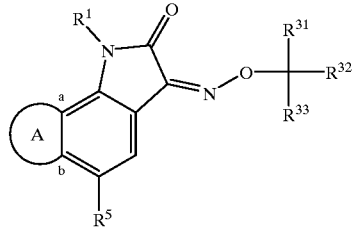

wherein
$R^1$ represents hydrogen, alkyl or benzyl; at least one of $R^{31}$, $R^{32}$, and $R^{33}$ independently represents hydrogen, alkyl, or hydroxyalkyl, and at least one of $R^{31}$, $R^{32}$, and $R^{33}$ independently represents $(CH_2)_n R^{34}$; wherein
$R^{34}$ represents hydroxy, carboxy, alkoxycarbonyl, alkenyloxycarbonyl, alkynyloxycarbonyl, cycloalkoxycarbonyl, cycloalkyl-alkoxycarbonyl, aryloxycarbonyl, aralkoxycarbonyl, or $CONR^{35}R^{36}$; wherein
$R^{35}$ and $R^{36}$ represents hydrogen, alkyl, alkenyl, alkynyl, hydroxyalkyl, cycloalkyl, aryl, aralkyl, or $(CH_2)_n$—$R^{37}$; wherein
$R^{37}$ represents hydroxy, carboxy, alkoxycarbonyl, alkenyloxycarbonyl, alkynyloxycarbonyl, cycloalkoxy-carbonyl, cycloalkyl-alkoxycarbonyl, aryloxycarbonyl, or aralkoxycarbonyl; or
$R^{35}$ and $R^{36}$ together with the N-atom to which they are attached form a saturated 5- to 6-membered, heterocyclic ring, optionally containing one additional N or O atom; and
n is 0, 1, 2, or 3; or
one of $R^{31}$, $R^{32}$, and $R^{33}$ represents hydrogen or alkyl, and two of $R^{31}$, $R^{32}$, and $R^{33}$ together form a lactone ring of the general formula (VI):

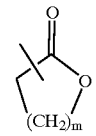

wherein m is 1, 2 or 3; and $R^5$ represents phenyl, naphthyl, thienyl, or pyridyl, all of which may be substituted one or more times with substituents selected from the group consisting of halogen, $CF_3$, $NO_2$, amino, alkyl, alkoxy, phenyl and $SO_2NR^{51}R^{52}$; wherein
$R^{51}$ and $R^{52}$ each independently represents hydrogen or alkyl; or $R^{51}$ and $R^{52}$ together with the N-atom to which they are attached form a saturated 4- to 7-membered, monocyclic, heterocyclic ring, optionally containing one additional N or O atom; and "A" represents a ring of five to seven atoms fused with the benzo ring at the positions marked "a" and "b", and formed by the following bivalent radicals:

a-$NR^6$—$CH_2$—$CH_2$-b;
a-$CH_2$—$NR^6$—$CH_2$-b;
a-$CH_2$—$CH_2$—$NR^6$-b;
a-$NR^6$—$CH_2$—$CH_2$—$CH_2$-b;
a-$CH_2$—$NR^6$—$CH_2$—$CH_2$-b;
a-$CH_2$—$CH_2$—$NR^6$—$CH_2$-b;
a-$CH_2$—$CH_2$—$CH_2$—$NR^6$-b;
a-$NR^6$—$CH_2$—$CH_2$—$CH_2$—$CH_2$-b;
a-$CH_2$—$NR^6$—$CH_2$—$CH_2$—$CH_2$-b;
a-$CH_2$—$CH_2$—$NR^6$—$CH_2$—$CH_2$-b;
a-$CH_2$—$CH_2$—$CH_2$—$NR^6$—$CH_2$-b; or
a-$CH_2$—$CH_2$—$CH_2$—$CH_2$—$NR^6$-b; wherein $R^6$ represents hydrogen, alkyl or $CH_2CH_2OH$;

or a pharmaceutically acceptable salt thereof.

In a more preferred embodiment, the indole-2,3-dione-3-oxime derivatives for use in the invention may be described by the general formula (V):

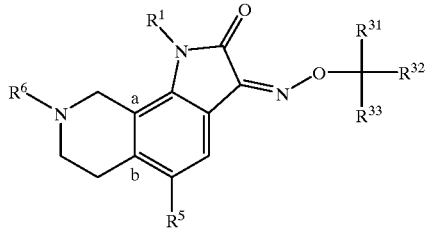

wherein $R^1$, $R^{31}$, $R^{32}$, $R^{33}$, $R^5$, and $R^6$ are as defined under formula IV above.

Definition of Substituents

In the context of this invention alkyl designates a straight chain or a branched chain containing of from one to six carbon atoms ($C_1$–$C_6$ alkyl), including but not limited to methyl, ethyl, propyl, isopropyl, butyl, isobutyl, t-butyl, pentyl and hexyl. In a preferred embodiment of this invention alkyl represents a $C_1$–$C_4$ alkyl, preferably a $C_1$–$C_3$ alkyl, most preferred methyl, ethyl, propyl or isopropyl.

In the context of this invention cycloalkyl designates a cyclic alkyl containing of from three to seven carbon atoms ($C_3$–$C_7$ cycloalkyl), including but not limited to cyclopropyl, cyclobutyl, cyclopentyl, and cyclohexyl.

In the context of this invention alkenyl designates a group containing of from two to six carbon atoms ($C_2$–$C_6$ alkenyl), including at least one double bond, for example, but not limited to ethenyl, 1,2- or 2,3-propenyl, 1,2-, 2,3-, or 3,4-butenyl.

In the context of this invention alkynyl designates a group containing of from two to six carbon atoms ($C_2$–$C_6$ alkynyl), including at least one triple bond, for example, but not limited to ethynyl, 1,2- or 2,3-propynyl, 1,2-, 2,3- or 3,4-butynyl.

In the context of this invention cycloalkyl-alkyl designates a cycloalkyl as defined above which is attached to an alkyl as also defined above, e.g. cyclopropylmethyl.

In the context of this invention aryl designates an aromatic hydrocarbon, such as phenyl or naphthyl.

In the context of this invention aralkyl designates an aryl as defined above which is attached to an alkyl as also defined above, e.g. benzyl.

In the context of this invention alkoxy designates an alkyl-O—, where alkyl is as defined above.

In the context of this invention alkoxycarbonyl designates an alkyl-O—CO—, where alkyl is as defined above.

In the context of this invention cycloalkoxycarbonyl designates a cycloalkyl-O—CO—, where cycloalkyl is as defined above.

In the context of this invention cycloalkyl-alkoxycarbonyl designates a cycloalkyl-alkyl-O—CO—, where cycloalkyl-alkyl is as defined above.

In the context of this invention alkenyloxycarbonyl designates an alkenyl-O—CO—, where alkenyl is as defined above.

In the context of this invention alkynyloxycarbonyl designates an alkynyl-O—CO—, where alkynyl is as defined above.

In the context of this invention aryloxycarbonyl designates an aryl-O—CO—, where aryl is as defined above.

In the context of this invention aralkoxycarbonyl designates an aralkyl-O—CO—, where aralkyl is as defined above.

In the context of this invention halogen represents fluorine, chlorine, bromine and iodine.

In the context of this invention amino represents $NH_2$, NH-alkyl, or N-(alkyl)$_2$, wherein alkyl is as defined above.

In a more specific aspect, the indole-2,3-dione-3-oxime derivatives of the invention is 8-methyl-5-(4-(N,N-dimethylsulfamoyl)phenyl)-6-7-8-9-tetrahydro-1H-pyrrolo[3,2-h]-isoquinoline-2,3-dione-3-O-(3-(2-oxo)tetrahydrofuryl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(5-(4-bromo-3-methoxy)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(5-(4-bromo-3-ethoxy)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(4-(N,5-dimethyl-3-oxo)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(4-(N-methyl-5-tertbutyl-3-oxo)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(4-(5-methyl-3-methoxy)isoxazolylmethyl)oxime; or 8-methyl-5-(4-(N,N-dimethylsulfamoyl)phenyl)-6-7-8-9-tetrahydro-1H-pyrrolo[3,2h]-isoquinoline-2,3-dione-3-O-(4-(5-methyl-3-ethoxy)isoxazolylmethyl)oxime;

or a pharmaceutically acceptable salt hereof.

In another specific embodiment, the indole-2,3-dione-3-oxime derivatives of the invention is 1-methyl-8-methyl-5-phenyl-6,7,8,9-tetrahydro-pyrrolo[3,2-h]isoquinoline -2,3-dione-3-O-(carboxymethyl)oxime;

1-methyl-8-methyl-5-phenyl-6,7,8,9-tetrahydro-1H-pyrrolo[3,2h]-isoquinoline-2,3-dione-3-O-(ethoxycarbonylmethyl)oxime;

1-methyl-8-methyl-5-(4-(N,N-dimethylsulfamoyl) phenyl)-6,7,8,9-tetrahydro-pyrrolo[3,2-h]isoquinoline-2,3-dione-3-O-(carboxymethyl)oxime;

1-methyl-8-methyl-5-(4-(N,N-dimethylsulfamoyl) phenyl)-6,7,8,9-tetrahydro-1H-pyrrolo[3,2-h] isoquinoline-2,3-dione-3-O-(1-ethoxycarbonyl-1-methylethyl)oxime;

1-methyl-8-methyl-5-(4-(N,N-dimethylsulfamoyl)
phenyl-6,7,8,9-tetrahydro-pyrrolo[3,2-h]isoquinoline-
2,3-dione-3-O-(ethoxycarbonylmethyl)oxime;

8-methyl-5-phenyl-6,7,8,9-tetrahydro-1H-pyrrolo[3,2-h]-
isoquinoline-2,3-dione-3-O-(carboxymethyl)oxime;

8-methyl-5-phenyl-6,7,8,9-tetrahydro-1H-pyrrolo[3,2-h]
isoquinoline-2,3-dione-3-O-(1-carboxy-1-methylethyl)
oxime;

8-methyl-5-phenyl-6,7,8,9-tetrahydro-1H-pyrrolo[3,2-h]
isoquinoline-2,3-dione-3-O-(ethoxycarbonylmethyl)
oxime;

8-methyl-5-phenyl-6,7,8,9-tetrahydro-1H-pyrrolo[3,2-h]
isoquinoline-2,3-dione-3-O-
(isopropoxycarbonylmethyl)oxime;

8-methyl-5-phenyl-6,7,8,9-tetrahydro-1H-pyrrolo[3,2-h]
isoquinoline-2,3-dione-3-O-(1-ethoxycarbonyl-1-
methyl)ethyloxime;

8-methyl-5-phenyl-6,7,8,9-tetrahydro-1H-pyrrolo[3,2-h]
isoquinoline-2,3-dione-3-O-(t-butoxycarbonylmethyl)
oxime;

8-methyl-5-phenyl-6,7,8,9-tetrahydro-1H-pyrrolo[3,2-h]
isoquinoline-2,3-dione-3-O-(N,N-
dimethylcarbamoylmethyl)oxime;

8-methyl-5-phenyl-6,7,8,9-tetrahydro-1H-pyrrolo[3,2-h]
isoquinoline-2,3-dione-3-O-(N-
methylcarbamoylmethyl)oxime;

8-methyl-5-phenyl-6,7,8,9-tetrahydro-1H-pyrrolo[3,2-h]
isoquinoline-2,3-dione-3-O-(N-
phenylcarbamoylmethyl)oxime;

8-methyl-5-phenyl-6,7,8,9-tetrahydro-1H-pyrrolo[3,2-h]
isoquinoline-2,3-dione-3-O-(N,N-di(2-hydroxyethyl)
carbamoylmethyl)oxime;

8-methyl-5-phenyl-6,7,8,9-tetrahydro-1H-pyrrolo[3,2-h]
isoquinoline-2,3-dione-3-O-
(morpholinocarbonylmethyl) oxime;

8-methyl-5-phenyl-6,7,8,9-tetrahydro-1H-pyrrolo[3,2-h]
isoquinoline-2,3-dione-3-O-
(ethoxycarbonylmethylcarbamoylmethyl)oxime;

8-methyl-5-phenyl-6,7,8,9-tetrahydro-1H-pyrrolo[3,2-h]
isoquinoline-2,3-dione-3-O-(N,N-di(2-(N,N-
diethylamino)ethyl)carbamoyl)oxime;

8-methyl-5-(4-(N,N-dimethylsulfamoyl)phenyl)-6,7,8,9-
tetrahydro-1H-pyrrolo[3,2-h]-isoquinoline-2,3-dione-
3-O-(carboxymethyl)oxime;

8-methyl-5-(4-(N,N-dimethylsulfamoyl)phenyl)-6,7,8,9-
tetrahydro-1H-pyrrolo[3,2-h]isoquinoline-2,3-dione-3-
O-(2-hydroxyethyl)oxime;

8-methyl-5-(4-(N,N-dimethylsulfamoyl)phenyl)-6,7,8,9-
tetrahydro-1H-pyrrolo[3,2-h]isoquinoline-2,3-dione-3-
O-(1-carboxy-1-methylethyl)oxime;

8-methyl-5-(4-(N,N-dimethylsulfamoyl)phenyl-6,7,8,9-
tetrahydro-1H-pyrrolo[3,2-h]isoquinoline-2,3-dione-3-
O-(ethoxycarbonylmethyl)oxime;

8-methyl-5-(4-(N,N-dimethylsulfamoyl)phenyl)-6,7,8,9-
tetrahydro-1H-pyrrolo[3,2-h]isoquinoline-2,3-dione-3-
O-(cyclopropylmethoxycarbonylmethyl)oxime;

8-methyl-5-(4-(N,N-dimethylsulfamoyl)phenyl)-6,7,8,9-
tetrahydro-1H-pyrrolo[3,2-h]isoquinoline-2,3-dione-3-
O-(isopropoxycarbonylmethyl)oxime;

8-methyl-5-(4-(N,N-dimethylsulfamoyl)phenyl)-6,7,8,9-
tetrahydro-1H-pyrrolo[3,2-h]isoquinoline-2,3-dione-3-
O-(N,N-dimethyl-carbamoylmethyl)oxime;

8-methyl-5-(4-(N,N-dimethylsulfamoyl)phenyl)-6,7,8,9-
tetrahydro-1H-pyrrolo[3,2-h]isoquinoline-2,3-dione-3-
O-(piperidinocarbonylmethyl)oxime;

8-methyl-5-(4-(piperidinosulfonyl)phenyl-6,7,8,9-
tetrahydro-1H-pyrrolo[3,2-h]isoquinoline-2,3-dione-3-
O-(piperidinocarbonylmethyl)oxime;

8-methyl-5-(4-(N,N-dimethylsulfamoyl)phenyl-6,7,8,9-
tetrahydro-1H-pyrrolo[3,2-h]isoquinoline-2,3-dione-3-
O-(morpholinocarbonylmethyl)oxime; or 8-methyl-5-(4-(N,N-dimethylsulfamoyl)phenyl)-6-7-8-9-
tetrahydro-1H-pyrrolo[3,2-h]isoquinoline-2,3-dione-3-
O-(4-hydroxybutyric acid-2-yl)oxime;

or a pharmaceutically acceptable salt hereof.

Steric Isomers

The chemical compounds for use in the invention may exist in (+) and (−) forms as well as in racemic forms. The use of racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds for use in the invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Moreover, some of the chemical compounds of the invention being oximes, may thus exist in two forms, syn- and anti-form (Z- and E-form), depending on the arrangement of the substituents around the —C=N-double bond. A chemical compound of the present invention may thus be the syn- or the anti-form (Z- and E-form), or it may be a mixture hereof.

Pharmaceutically Acceptable Salts

The indole-2,3-dione-3-oxime derivatives for use in the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulfonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound for use in the invention includes alkali metal salts, such as the sodium salt of a chemical compound for use in the invention containing a carboxy group.

The chemical compound for use in the invention may be provided in solved or dissolved form together with a pharmaceutically acceptable solvents such as water, ethanol and the like. In general, solved forms are considered equivalent to dissolved forms for the purposes of this invention.

Pharmaceutical Compositions

In another aspect the invention provides the use of pharmaceutical compositions comprising a therapeutically effective amount of the chemical compound of the invention. While a chemical compound of the invention for use in therapy may be administered in the form of the raw chemical compound, it is preferred to introduce the active ingredient, optionally in the form of a physiologically acceptable salt, in a pharmaceutical composition together with one or more excipients, carriers and/or diluents.

Pharmaceutical compositions for use in the method of the invention comprise the chemical compound of formula I, or a pharmaceutically acceptable salt or derivative thereof, together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), vaginal or parenteral (including intramuscular, subcutaneous and intravenous) administration, or in a form suitable for administration by inhalation or insufflation.

The chemical compound for use in the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Compositions containing ten (10) milligrams of active ingredient or, more broadly, 0.1 to one hundred (100) milligrams, per tablet, are accordingly suitable representative unit dosage forms The chemical compound for use in the invention can be administered in a wide variety of oral and parenteral dosage forms. It will be obvious to those skilled in the art that the following dosage forms may comprise, as the active component, either a chemical compound of formula I or a pharmaceutically acceptable salt thereof.

For preparing pharmaceutical compositions from a chemical compound of formula I, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound for use according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

It is at present contemplated that a suitable dosage is in the range of from about 0.1 to about 1000 mg of the pure chemical compound per day, more preferred of from about 10 to about 500 mg of the pure chemical compound per day, most preferred of from about 30 to about 100 mg of the pure chemical compound per day, dependent i.a. upon the exact mode of administration, the form in which administered, the indication toward which the administration is directed, the subject involved and the body weight of the subject involved, and further the preference and experience of the physician or veterinarian in charge.

Methods of Preparation

The indole-2,3-dione-3-oxime derivatives for use in the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

The chemical compounds for use in the invention may be prepared by reacting a compound having the general formula

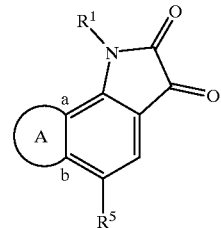

wherein $R^1$, $R^5$, and "A" have the meanings set forth above, with a compound having the formula

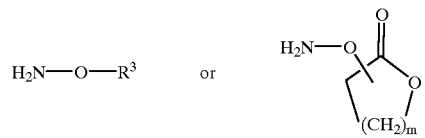

wherein $R^3$ and m have the meanings set forth above, optionally followed by converting the thus obtained compound to another compound for use in the invention or to a pharmaceutically acceptable salt hereof by using conventional methods.

EXAMPLES

The invention is further illustrated with reference to the following examples which are not intended to be in any way limiting to the scope of the invention as claimed.

Example 1

Preparatory Example

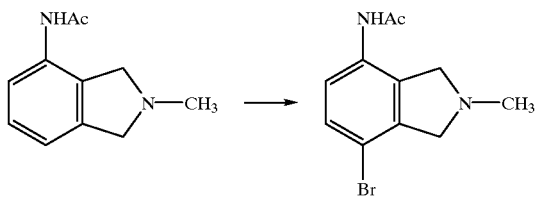

A solution of 4-acetamido-2-methyl-2H-1,3-dihydro-isoindole (10 g) and bromine (3.0 g) in trifluoroacetic acid (150 ml) was stirred at 50° C. for 40 hours. The solution was evaporated in vacuo. The residue was dissolved in water (300 ml), and pH was adjusted to neutral with sat. $Na_2CO_3$. This treatment afforded a crystalline precipitate of the product, which was collected by filtration. Yield 9 g, m.p. 145°–148°.

Example 2

Preparatory Example

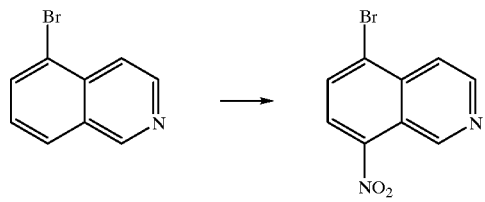

A solution of potassium nitrate (1.78 g, 8.56 mmol) was added slowly to a solution of 5-bromoisoquinoline in 12 mL $H_2SO_4$. After stirring for 3 hours the reaction mixture was poured onto ice and neutralised with conc. ammonium hydroxide. The yellow precipitate was extracted with ethyl acetate (3×), and the combined organic layers were washed with saturated NaCl, dried over $MgSO_4$, filtered and concentrated. The residue was chromatographed on silica gel (40% ethyl acetate in hexane as eluent) to give 5-bromo-8-nitroisoquinoline in 96% yield.

Example 3

Preparatory Example

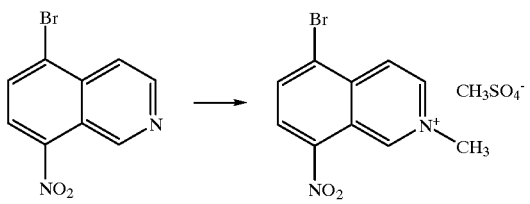

A mixture of 5-bromo-8-nitroisoquinoline (0.99 g, 3.91 mmol) and dimethylsulfate (0.41 mL) in anhydrous DMF (20 mL) was heated at 80° C. for 24 hours. After removing the DMF in vacuo, the isoquinoline methylammonium salt was obtained (used without further purification).

In a similar manner the following compound was prepared:

2-ethyl-5-bromo-8-nitroquinolinium ethylsulphate by reaction with diethyl sulphate.

Example 4

Preparatory Example

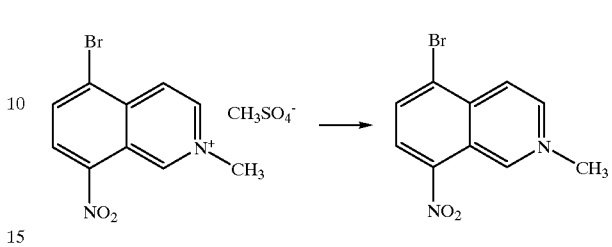

The isoquinoline salt (3.9 mmol) was dissolved in acetic acid (10 mL) and sodium borohydride (0.15 g, 3.97 mmol) was added. After stirring for 24 h, the reaction mixture was diluted with a mixture of ethyl acetate and water and potassium carbonate was added portion-wise to neutralise the acetic acid. The aqueous layer was extracted with ethyl acetate (2×), washed with saturated NaCl, dried over $MgSO_4$, filtered and evaporated. The residue was chromatographed on silica gel (30% ethyl acetate in hexane as eluent) to give the light sensitive N-methyl 5-bromo-8-nitro-1,2,3,4-tetrahydroisoquinoline (0.47 g, 45% yield).

N-ethyl-5-bromo-8-nitro-1,2,3,4-tetrahydroisoquinoline was prepared according to the same procedure. M.p. 52–53° C.

Example 5

Preparatory Example

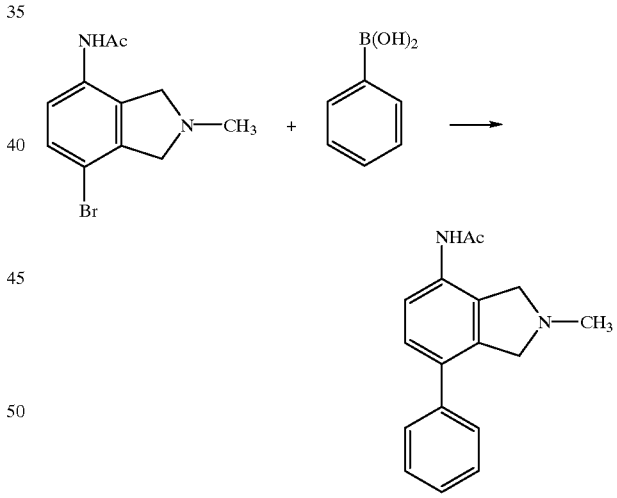

A mixture of 4-acetamido-7-bromo-2-methyl-2H-1,3-dihydro-isoindole (0.2 g), phenyl boronic acid (137 mg), tetrakis(triphenylphosphine)palladium [0] (26 mg), $NaHCO_3$, (315 mg) was stirred at reflux temperature in a mixture of water (3.75 ml) and dimethoxyethane (7.5 ml) for 90 min. After cooling to room temperature the reaction mixture was partitioned between EtOAc (25 ml) and aq. NaOH (2×5 ml, 1N). The organic phase was then dried over $Na_2SO_4$ and evaporated to give 4-acetamido-7-phenyl-2-methyl-2H-1,3-dihydro-isoindole, m.p. 160–62° C.;

In a similar manner the following compounds were prepared from the appropriate bromides and boronic acids:

4-acetamido-7-phenyl-2-ethyl-2H-1,3-dihydro-isoindole, m.p. 67–68° C.;

4-acetamido-7-(1-naphthyl)-2-methyl-2H-1,3-dihydro-isoindole m.p. 260–62° C.;

4-acetamido-5-nitro-7-phenyl-2-methyl-2H-1,3-dihydro-isoindole m.p. 270–72° C.;

5-acetamido-2-methyl-6-nitro-8-phenyl-1,2,3,4-tetrahydro-isoquinoline m.p. 214–217° C.;

2-methyl-5-phenyl-8-nitro-1,2,3,4-tetrahydro-isoquinoline m.p. 75–78° C. (from reaction between phenyl boronic acid and 5-bromo-2-methyl-8-nitro-1,2,3,4-tetrahydro-isoquinoline);

2-methyl-5-(4-chlorophenyl)-8-nitro-1,2,3,4-tetrahydro-isoquinoline m.p. 162–163° C.;

2-methyl-5-(4-trifluoromethylphenyl)-8-nitro-1,2,3,4-tetrahydro-isoquinoline m.p. 133–134° C.

2-methyl-5-(4-fluorophenyl)-8-nitro-1,2,3,4-tetrahydro-isoquinoline m.p. 159–160° C.

5-acetamido-2-methyl-8-phenyl-1,2,3,4-tetrahydro-isoquinoline, m.p. 140–143° C.

Example 6

Preparatory Example

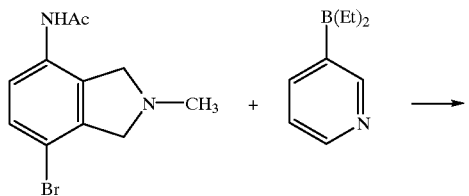

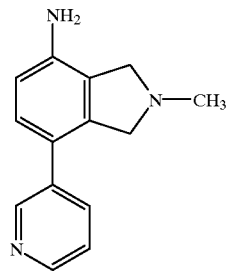

A mixture of 4-acetamido-7-bromo-2-methyl-2H-1,3-dihydro-isoindole(8 mmol), diethyl(3-pyridyl)borane, tetrakis(triphenylphosphine)palladium (0) (400 mg), powdered potassium hydroxide (32 mmol) and tetrabutylammonium bromide (4 mmol) was refluxed in THF (50 mL) for 48 hours. The mixture was then cooled to room temperature, where after EtOAc (100 mL) was added. The resulting mixture was then filtered through filter aid, and the filtrate was evaporated. The residue was partitioned between water (50 mL) and diethyl ether (25 mL). This treatment afforded a crystalline precipitate of the product which was collected by filtration and washed with water and diethylether, m.p. 180–86° C.

Example 7

Preparatory Example

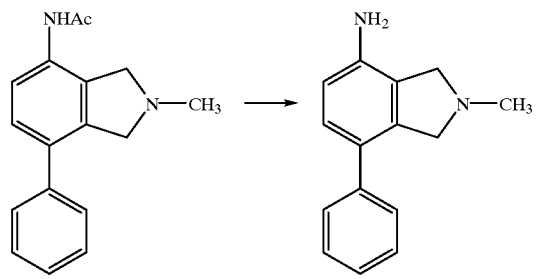

4-acetamido-7-phenyl-2-methyl-2H-1,3-dihydro-isoindole (2.6 g) was heated with stirring at 80° C. for 48 hours in sulphuric acid (66%, 25 mL), where after the solution was poured onto ice and then neutralised with aq. NaOH. The precipitated product was collected by filtration, and washed with water. M.p. 154–55° C.

Similar deacetylations gave:

4-amino-7-(1-naphthyl)-2-methyl-2H-1,3-dihydro-isoindole, m.p. 145–48° C.;

4-amino-5-nitro-7-phenyl-2-methyl-2H-1,3-dihydro-isoindole, m.p. 170–72° C.;

5-amino-2-methyl-6-nitro-8-phenyl-1,2,3,4-tetrahydro-isoquinoline, m.p. 128–130° C.;

4-amino-7-phenyl-2-ethyl-2H-1,3-dihydro-isoindole hydrochloride, m.p. 222–225° C.; and 5-amino-2-methyl-8-phenyl-1,2,3,4-tetrahydro-isoquinoline, m.p. 273–275° C.

Example 8

Preparatory Example

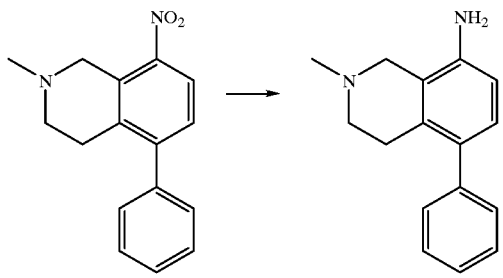

8-amino-2-methyl-5-phenyl-1,2,3,4-tetrahydro-isoquinoline hydrochloride, m.p. 210–21° C., 8-amino-2-methyl-5-(4-fluorophenyl)-1,2,3,4-tetrahydro-isoquinoline, m.p. 141° C., 8-amino-2-methyl-5-(4-trifluoromethylphenyl)-1,2,3,4-tetrahydro-isoquinoline, m.p. 132–134° C., and 8-amino-2-methyl-5-(4-chlorophenyl)-1,2,3,4-tetrahydro-isoquinoline hydrochloride, m.p. 213–215° C., were all obtained by hydrogenation using Pd/C as catalyst and ethanol as solvent.

Example 9

Preparatory Example

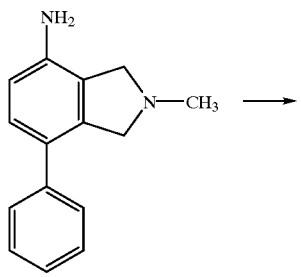 →

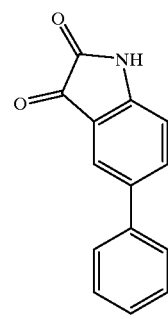

A mixture of 4-amino-7-phenyl-2-methyl-2H-1,3-dihydro-isoindole (2.0 g, 9 mmol), conc. HCl (0.83 ml), 1.5 ml chloral, 10 g of $Na_2SO_4$, $NH_2OH$ (2.0 g) in water (60 mL) was refluxed for two hours, whereafter it was cooled and neutralised with sat. $NaHCO_3$. The aqueous solution was decanted from the oily residue which was dissolved in methylene chloride (100 mL). This solution was dried over $Na_2SO_4$, and the solvent was removed by evaporation. The residue was dissolved in methane sulphonic acid (3 ml) and heated to 120° C. for 30 min. After cooling to ambient temperature the solution was diluted with water (20 mL) and neutralised with sat. $Na_2CO_3$. The impure product was filtered off. Pure 7-methyl-5-phenyl-1,6,7,8-tetrahydrobenzo[2,1-b:3,4-c]dipyrrole-2,3-dione m.p. 187–90° C. was obtained after column purification on silica gel using methylene chloride acetone methanol (4:1:1) as eluent.

In a similar manner the following compounds were prepared:

7-ethyl-5-phenyl-1,6,7,8-tetrahydrobenzo[2,1-b:3,4-c] dipyrrole-2,3-dione, m.p. >250° C. (decomposes);

7-methyl-5-(1-naphthyl)-1,6,7,8-tetrahydrobenzo[2,1-b:3,4-c]dipyrrole-2,3-dione-3-oxime in low yield, m.p.>300° C.;

7-methyl-5-(3-pyridyl)-1,6,7,8-tetrahydrobenzo[2,1-b:3,4-c]dipyrrole-2,3-dione-3-oxime. NMR ($^1$H,500 MHz, 6-D DMSO):2.5 ppm (3H,S), 3.8 ppm (2H,S), 3.9 ppm (2H,S), 6.5–8.7 ppm (5H aromatic, 1S, 4M), 11.0 ppm (1H,S, NH) 13.4 ppm (1H,S,NOH);

8-methyl-5-phenyl-6,7,8,9-tetrahydro-1H-pyrrolo[3,2-h] isoquinoline-2,3-dione, m.p. 280–82° C.;

8-methyl-5-(4-chlorophenyl)-6,7,8,9-tetrahydro-1H-pyrrolo[3,2-]isoquinoline-2,3-dione, m.p. 225° C. (decomposes);

8-methyl-5-(4-trifluoromethylphenyl)-6,7,8,9-tetrahydro-1H-pyrrolo[3,2-h]isoquinoline-2,3-dione, m.p. 220–25° C.;

8-methyl-5-(4-fluorophenyl)-6,7,8,9-tetrahydro-1H-pyrrolo[3,2-h]isoquinoline-2,3-dione, m.p. 220–21° C.; and 7-methyl-5-phenyl-6,7,8,9-tetrahydro-1H-pyrrolo[2,3-f] isoquinoline-2,3-dione, m.p.>300° C.

Example 10

Preparatory Example

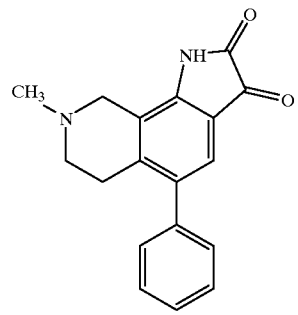

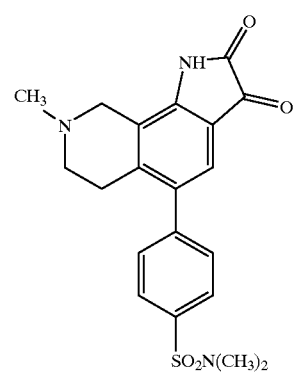

4 g of 8-methyl-5-phenyl-6,7,8,9-tetrahydro-1H-pyrrolo [3,2-h]isoquinoline-2,3-dione was added in portions to ice-cold chlorosulphonic acid (20 ml). The solution was allowed to stir at room temperature for ½ hour before it was cooled on ice. Excess chlorosulphonic acid was then destroyed carefully with water. After addition of 40 ml of water a heavy precipitate of the sulphonyl chloride was obtained. This solid was filtered off and washed with water whereafter, without drying, it was dissolved in tetrahydrofuran (100 ml). To this solution was drop-wise added a solution of dimethylamine in tetrahydrofuran(100 ml, 0,5M). The final mixture was stirred at room temperature for 3 hours and then evaporated. The oily residue was partitioned between water/Ethyl acetate. The organic phase was extracted with 100 ml 0,5N hydrochloric acid. The aqueous phase was separated and pH adjusted to 9. This caused a precipitate of crude product which could be purified by column cromatography.

8-methyl-5-(4-(piperidinosulfonyl)phenyl)-6,7,8,9-tetrahydro-1H-pyrrolo[3,2-h]isoquinoline-2,3-dione, m.p.>300° C. was prepared analogously.

Example 11

Preparatory Example

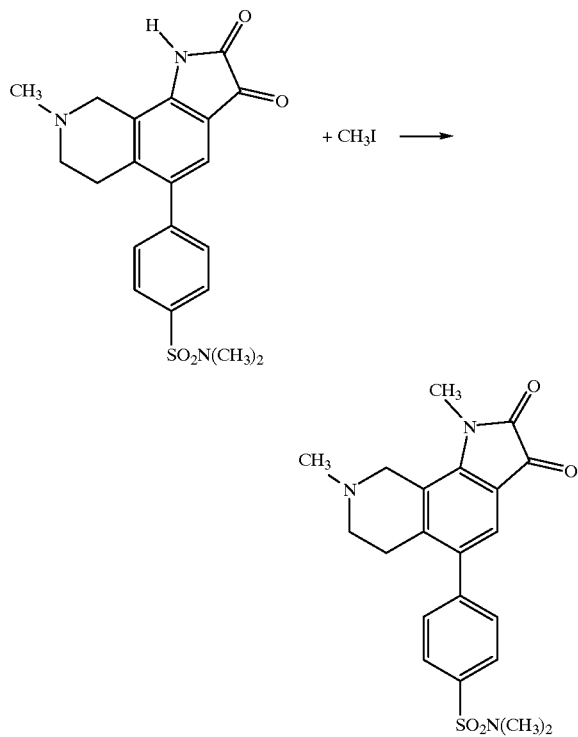

NaH 60% (110 mg, 2.8 mmol) was added at 0° C. to a mixture of 8-methyl-5-(4-(N,N-dimethylsulfamoyl)phenyl)-6,7,8,9-tetrahydro-1-H-pyrrolo[3,2-h]isoquinoline-2,3-dione (1 g, 2.5 mmol) in dimethylformamide (10 ml). The mixture was stirred at 0° C. for 10 min. Methyliodide (175 μl, 2.8 mmol) was added and the mixture was stirred for one hour at ambient temperature. The reaction mixture was poured into water (20 ml) and extracted with ethyl acetate (2×25 ml). The organic phase was dried over sodium sulphate and evaporated. Pure 1-methyl-8-methyl-5-(4-(N,N-dimethylsulfamoyl)phenyl)-6,7,8,9-tetrahydro-pyrrolo[3,2-h]isoquinoline-2,3-dione was obtained after purification on silica gel using dichloromethane/acetone/methanol (8:1:1) as the eluent. Yield 160 mg, m.p. 232–240° C. (decomposes).

The following compound was obtained analogously:

1-methyl-8-methyl-5-phenyl-6,7,8,9-tetrahydro-pyrrolo[3,2-h]isoquinoline-2,3-dione.

Example 12

Preparatory Example

1)

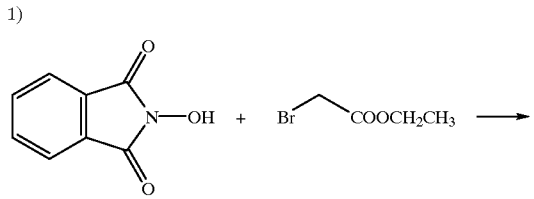

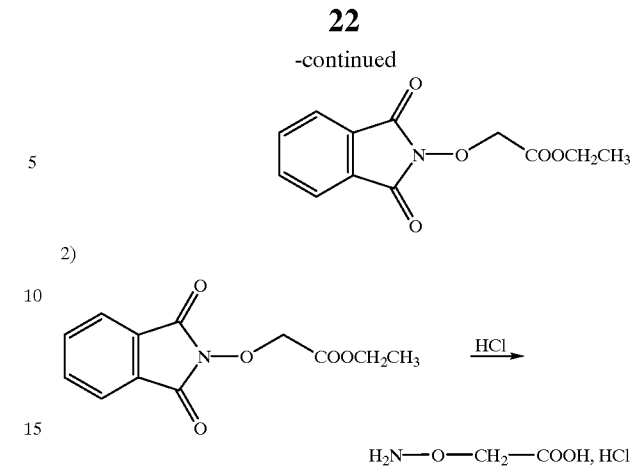

1a) To a solution of N-hydroxyphtalimide (48.9 g, 305.37 mmol) and ethyl 2-bromoacetate (51.0 ml, 459.8 mmol) in dry dimethylformamide (500 ml) was added triethylamine (84.6 ml, 610.74 mmol) and the mixture was stirred at room temperature overnight. The precipitate was filtered off and washed with dimethylformamide. The filtrate was evaporated and the residue was stirred with diluted hydrochloric acid (450 ml, 0.7M). The precipitate was filtered off and dried. Yield: 72.4 g.

1b) The compound N-(2-bromoethoxy)phtalimide was prepared analogously from 1,2-dibromoethane and N-hydroxyphtalimide.

2a) The product obtained under a) above (72.0 g, 288.9 mmol) was suspended in 6M HCL (720 ml). The mixture was stirred at 100° C. for 1.5 hours. The mixture was allowed to cool to room temperature with stirring. The precipitate was filtered off and the filtrate was concentrated by evaporation. To the residue was added toluene and the mixture was evaporated to dryness. The residue thus obtained was then stirred with a mixture of toluene and ethyl acetate. This treatment resulted in precipitation of the product which was filtered off and dried. The filtrate was evaporated to dryness and the residue was triturated with methanol. This afforded a precipitate of the product which was filtered off and dried. Total yield is 25.6 g.

2b) The compound O-(2-hydroxyethyl)hydroxylamine hydrochloride was prepared analogously from the compound obtained under 1 b) above.

Example 13

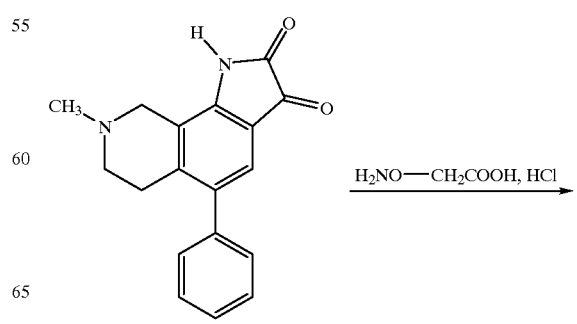

23

-continued

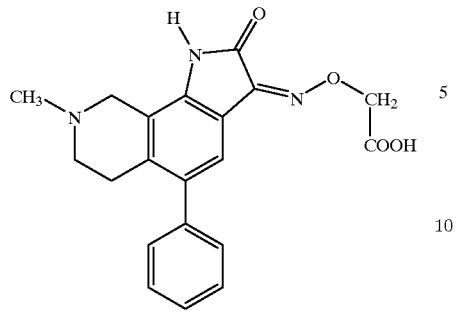

A suspension of 8-methyl-5-phenyl-6,7,8,9-tetrahydro-1H-pyrrolo[3,2-h]isoquinoline-2,3-dione (2.6 g, 8 mmol) in water (75 ml) was heated to reflux. The product of example 12 (2a) (1,1 g, 8.7 mmol) was added and heating was continued for 30 min. After cooling to room temperature, the precipitated product was filtered off.

8-methyl-5-phenyl-6,7,8,9-tetrahydro-1H-pyrrolo[3,2-h]-isoquinoline-2,3-dione-3-O-(carboxymethyl)oxime, yield 3.27 g, m.p. 283–285° C. (decomposes).

The following compounds were prepared analogously:

8-methyl-5-(4-(N,N-dimethylsulfamoyl)phenyl)-6,7,8,9-tetrahydro-1H-pyrrolo[3,2-h]-isoquinoline-2,3-dione-3-O-(carboxymethyl)oxime hydrochloride, m.p.>338° C. (decomposes);

1-methyl-8-methyl-5-phenyl-6,7,8,9-tetrahydro-pyrrolo[3,2-h]isoquinoline-2,3-dione-3-O-(carboxymethyl)oxime hydrochloride, m.p. 180–194° C. (decomposes);

1-methyl-8-methyl-5-(4-(N,N-dimethylsulfamoyl)phenyl)-6,7,8,9-tetrahydro-pyrrolo[3,2-h]isoquinoline-2,3-dione-3-O-(carboxymethyl)oxime hydrochloride, m.p. 277–285° C. (decomposes);

8-methyl-5-(4-(N,N-dimethylsulfamoyl)phenyl)-6,7,8,9-tetrahydro-1H-pyrrolo[3,2-h]isoquinoline-2,3-dione-3-O-(2-hydroxyethyl)oxime, m.p. 163° C. (decomposes);

1-methyl-8-methyl-5-(4-(N,N-dimethylsulfamoyl)phenyl)-6,7,8,9-tetrahydro-1H-pyrrolo[3,2-h]isoquinoline-2,3-dione-3-O-(1-ethoxycarbonyl-1-methylethyl)oxime methanesulfate, m.p. 250° C. (decomposes);

8-methyl-5-(4-(N,N-dimethylsulfamoyl)phenyl)-6,7,8,9-tetrahydro-1H-pyrrolo[3,2-h]isoquinoline-2,3-dione-3-O-(1-carboxy-1-methylethyl)oxime hydrochloride, m.p. 250° C. (decomposes; dark at 220° C.); and 8-methyl-5-phenyl-6,7,8,9-tetrahydro-1H-pyrrolo[3,2-h]isoquinoline-2,3-dione-3-O-(1-carboxy-1-methylethyl)oxime hydrochloride, m.p. 250° C. (decomposes; dark at 220° C.).

24

Example 14

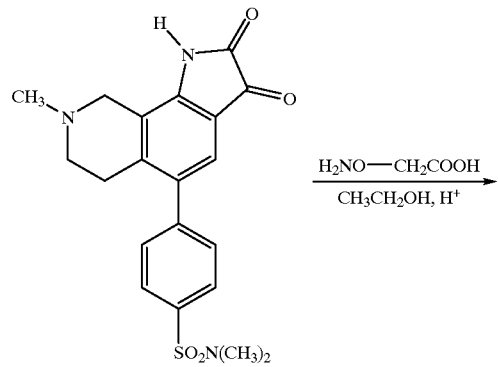

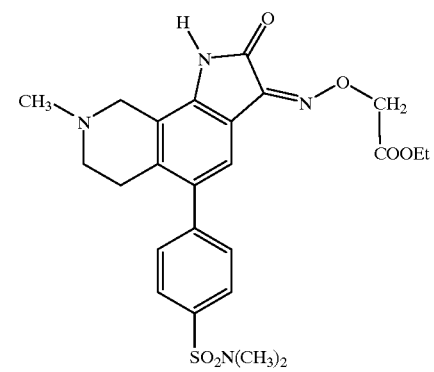

8-methyl-5-(4-(N,N-dimethylsulfamoyl)phenyl)-6,7,8,9-tetrahydro-1H-pyrrolo[3,2h]-isoquinoline-2,3-dione (3.0 g, 7.5 mmol) in dry ethanol (50 ml) was heated to reflux. The compound of example 12 (2.4 g, 18.8 mmol) and HCl in ether (2-3 ml, 0.9M) was added and reflux was continued for 48 hours. Additional HCl in ether was added at intervals during the this period. The mixture was evaporated and the residue was stirred with water and neutralised with saturated NaHCO$_3$. The mixture was filtered and pure 8-methyl-5-(4-(N,N-dimethylsulfamoyl)phenyl)-6,7,8,9-tetrahydro-1H-pyrrolo[3,2h]-isoquinoline-2,3-dione-3-O-(ethoxycarbonylmethyl)oxime was obtained after purification on silica gel using dichloromethane/methanol/acetone/(4:1:1) as eluent.

The compound 1-methyl-8-methyl-5-phenyl-6,7,8,9-tetrahydro-1H-pyrrolo[3,2h]-isoquinoline-2,3-dione-3-O-(ethoxycarbonylmethyl)oxime hydrochloride, m.p. 271–275° C. (decomposes) was prepared analogously.

Example 15

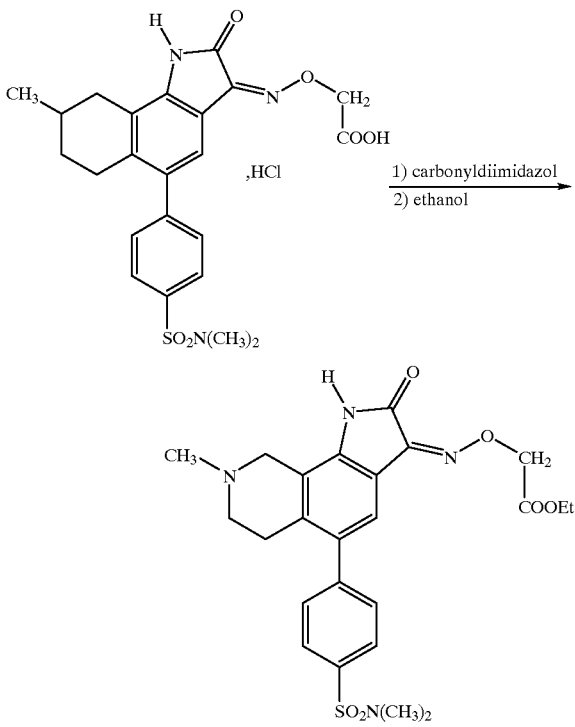

8-methyl-5-(4-(N,N-dimethylsulfamoyl)phenyl-6,7,8,9-tetrahydro-1H-pyrrolo[3,2-h]isoquinoline-2,3-dione-3-O-(carboxymethyl)oxime, HCl (1 g, 2.1 mmol) was heated to reflux in dry tetrahydrofuran (50 ml). Carbonyldiimidazole (3×4 g, 9.5 mmol) was added at 15 min intervals. Following the addition of carbonyldiimidazole, reflux was continued for 30 min. After cooling, dry ethanol (1 ml, 16 mmol) was added and the mixture was stirred at room temperature overnight. The solvent was removed by evaporation. The residue was stirred with water and NaHCO₃. The resulting crystalline product, 8-methyl-5-(4-(N,N-dimethylsulfamoyl)phenyl-6,7,8,9-tetrahydro-1H-pyrrolo[3,2-h]isoquinoline-2,3-dione-3-O-(ethoxycarbonylmethyl)oxime, was filtered off and dried. M.p.>300° C. (decomposes).

The following compounds were prepared analogously:

8-methyl-5-phenyl-6,7,8,9-tetrahydro-1H-pyrrolo[3,2-h]isoquinoline-2,3-dione-3-O-(ethoxycarbonylmethyl)oxime, m.p. 294° C. (decomposes);

8-methyl-5-phenyl-6,7,8,9-tetrahydro-1H-pyrrolo[3,2-h]isoquinoline-2,3-dione-3-O-(isopropoxycarbonylmethyl)oxime, m.p. 174–176° C. (decomposes);

8-methyl-5-phenyl-6,7,8,9-tetrahydro-1H-pyrrolo[3,2-h]isoquinoline-2,3-dione-3-O-(1-ethoxycarbonyl-1-methyl)ethyloxime, m.p. 159–169° C.;

1-methyl-8-methyl-5-(4-(N,N-dimethylsulfamoyl)phenyl-6,7,8,9-tetrahydro-pyrrolo[3,2-h]isoquinoline-2,3-dione-3-O-(ethoxycarbonylmethyl)oxime, m.p. 287–300° C. (decomposes);

8-methyl-5-phenyl-6,7,8,9-tetrahydro-1H-pyrrolo[3,2-h]isoquinoline-2,3-dione-3-O-(t-butoxycarbonylmethyl)oxime, m.p. 295° C. (176° C. decomposes);

8-methyl-5-phenyl-6,7,8,9-tetrahydro-1H-pyrrolo[3,2-h]isoquinoline-2,3-dione-3-O-(N,N-dimethylcarbamoylmethyl)oxime, m.p. 194–196° C.;

8-methyl-5-phenyl-6,7,8,9-tetrahydro-1H-pyrrolo[3,2-h]isoquinoline-2,3-dione-3-O-(N-methylcarbamoylmethyl)oxime, m.p. 219–221° C.;

8-methyl-5-phenyl-6,7,8,9-tetrahydro-1H-pyrrolo[3,2-h]isoquinoline-2,3-dione-3-O-(N-phenylcarbamoylmethyl)oxime, m.p. 208–210° C.;

8-methyl-5-phenyl-6,7,8,9-tetrahydro-1H-pyrrolo[3,2-h]isoquinoline-2,3-dione-3-O-(N,N-di(2-hydroxyethyl)carbamoylmethyl)oxime, m.p. 136–144° C.; (decomposes);

8-methyl-5-phenyl-6,7,8,9-tetrahydro-1H-pyrrolo[3,2-h]isoquinoline-2,3-dione-3-O-(morpholinocarbonylmethyl)oxime, m.p. 216–217° C.;

8-methyl-5-phenyl-6,7,8,9-tetrahydro-1H-pyrrolo[3,2-h]isoquinoline-2,3-dione-3-O-(ethoxycarbonylmethylcarbamoylmethyl)oxime, m.p. 170–172° C.;

8-methyl-5-phenyl-6,7,8,9-tetrahydro-1H-pyrrolo[3,2-h]isoquinoline-2,3-dione-3-O-(N,N-di(2-(N,N-diethylamino)ethyl)carbamoyl)oxime, oil;

8-methyl-5-(4-(N,N-dimethylsulfamoyl)phenyl-6,7,8,9-tetrahydro-1H-pyrrolo[3,2-h]isoquinoline-2,3-dione-3-O-(cyclopropylmethoxycarbonylmethyl)oxime, m.p. 143–145° C.;

8-methyl-5-(4-(N,N--dimethylsulfamoyl)phenyl-6,7,8,9-tetrahydro-1H-pyrrolo[3,2-h]isoquinoline-2,3-dione-3-O-(isopropoxycarbonylmethyl)oxime, m.p.>300° C.;

8-methyl-5-(4-(N,N-dimethylsulfamoyl)phenyl-6,7,8,9-tetrahydro-1H-pyrrolo[3,2-h]isoquinoline-2,3-dione-3-O-(N,N-dimethyl-carbamoylmethyl)oxime, m.p. 183–185° C.;

8-methyl-5-(4-(N,N-dimethylsulfamoyl)phenyl-6,7,8,9-tetrahydro-1H-pyrrolo[3,2-h]isoquinoline-2,3-dione-3-O-(piperidinocarbonylmethyl)oxime methane sulphate, m.p. 200–211° C. (decomposes);

8-methyl-5-(4-(piperidinosulfonyl)phenyl-6,7,8,9-tetrahydro-1H-pyrrolo[3,2-h]isoquinoline-2,3-dione-3-O-(piperidinocarbonylmethyl)oxime methane sulphate, m.p. 195–215° C. (decomposes); and 8-methyl-5-(4-(N,N-dimethylsulfamoyl)phenyl-6,7,8,9-tetrahydro-1H-pyrrolo[3,2-h]isoquinoline-2,3-dione-3-O-(morpholinocarbonylmethyl)oxime, m.p. 222–224° C.

Example 16

Preparatory Example
3-Methoxy-5-methylisoxazole

To a solution of 3-hydroxy-5-methylisoxazole (13.5 g, 136 mmol) in ether (100 mL) was added diazomethane until a persistent yellow colour was obtained. The reaction was stirred for another 30 min at room temperature. The ether was evaporated off and the residue purified by column chromatography on silica gel using ether as eluent. 9 g of the desired material was obtained.

Example 17

Preparatory Example
3-Hydroxy-4,5-dimethylisoxazole

To a solution of hydroxylamine hydrochloride (12.1 g, 0.17 mol) in methanol/water (1:5, 60 mL) was added sodium hydroxide (7.7 g, 0.19 mol) in 20 mL water. The reaction was cooled to −70° C. and filtered. The cold (−70° C.) filtrate was added to a cold (−70° C.) solution of ethyl-2-methylacetoacetate (12.5 g, 87 mmol) and sodium hydroxide (3.6 g, 90 mmol) in methanol/water (1:5, 60 mL). The reaction was stirred at −70° C. for another 2 hr. Acetone (13 mL) was added and the reaction poured into 10% aqueous hydrochloric acid heated to 80° C. The final mixture was kept at 75–80° C. for another 30 min. Extraction with ether (6×150 mL), drying of the combined extracts over magnesium sulphate and subsequent filtration and evaporation of the solvent afforded 8.1 g of the desired material.

The following compound was prepared analogously:

3-hydroxy-4-methyl-5-tertbutylisoxazole.

Example 18

Preparatory Example
N,4,5-trimethyl-3-isoxazolone

To a solution of 3-hydroxy-4,5-dimethylisoxazole (7 g, 62 mmol) in ether (50 mL) was added diazomethane until a persistent yellow colour was obtained. The reaction was stirred for another 30 min at room temperature. The ether was evaporated off and the residue purified by column chromatography on silica gel using ether as eluent. 4 g of the desired material was obtained.

The following compounds were prepared analogously:

N,4-dimethyl-5-tertbutyl-3-isoxazolone; and 3-methoxy-4,5-dimethylisoxazolone.

Example 19

Preparatory Example
3-Methoxy-4-bromo-5-bromomethyl-isoxazole

To a solution of 3-methoxy-5-methylisoxazole (9 g, 79.6 mmol), heated to reflux, in tetrachloromethane (120 mL) was added N-bromosuccinimide (17.7 g, 99.5 mmol) in four portions over 2 hours. Catalytic amounts of benzoylperoxide was added at the same time as the first and the third portion of N-bromosuccinimide. The reaction was cooled to 10° C. and filtered. The filtrate was evaporated to dryness and the residue purified by column chromatography on silica gel using petroleum ether/ether (3:2) as eluent. 10 g of the desired material was obtained.

The following compounds were prepared analogously:

4-bromomethyl-N,5-dimethyl-3-isoxazolone;

4-bromomethyl-N-methyl-5-tertbutyl-3-isoxazolone; and 4-bromomethyl-3-methoxy-5-methylisoxazole.

Example 20

Preparatory Example
α-Phthalimidooxy-γ-butyrolactone, hydrochloride

To a solution of α-Bromo-γ-butyrolactone (3.0 mL, 36 mmol) in dimethylformamide (50 mL) was added N-hydroxyphthalimide (4.6 g, 28 mmol) followed by triethylamine (7.7 mL, 56 mmol). After stirring for 4 hours at room temperature the reaction was filtered and evaporated to dryness using an oil pump. Hydrochloric acid (1M, 28 mL) and water (20) mL) was added. The precipitate was filtered off and washed with water. Drying in the air gave 7.1 g of beige crystals.

The following compounds were prepared analogously:

4-bromo-3-methoxy-5-phthalimidooxymethylisoxazole;

N,5-dimethyl-4-phthalimidooxymethyl-3-isoxazolone;

N-methyl-4-phthalimidooxymethyl-5-tertbutyl-3-isoxazolone; and 4-phthalimidooxymethyl-3-methoxy-5-methylisoxazole.

Example 21

Preparatory Example
α-Aminooxy-γ-butyrolactone hydrochloride

α-Phthalimidooxy-γ-butyrolactone (1.0 g, 4 mmol) was added to hydrochloric acid (1M, 10 mL) at reflux. After 5 min. at reflux for 5 min and the reaction was cooled down on an ice bath and filtered. The filtrate was evaporated to dryness. Toluene was added and residual water removed azeotropic distillation. 0.75 g of the desired material was obtained.

The following compounds were prepared analogously:

4-bromo-3-methoxy-5-aminooxymethylisoxazole hydrochloride;

N,5-dimethyl-4-aminooxymethyl-3-isoxazolone hydrochloride;

N-methyl-4-aminooxymethyl-5-tertbutyl-3-isoxazolone hydrochloride; and 4-aminooxymethyl-3-methoxy-5-methylisoxazole hydrochloride.

Example 22

To a solution of 8-methyl-5-(4-(N,N-dimethylsulfamoyl)phenyl)-6-7-8-9-tetrahydro-1H-pyrrolo[3,2-h]isoquinoline-2,3-dione (1.06 g, 2.7 mmol) in methanol (30 mL) heated to reflux, was added α-aminooxy-γ-butyrolactone (0.75 g, 4 mmol) dissolved in warm methanol (10 mL). Yellow crystals precipitate out. The reaction was heated at reflux for another 15 min and cooled to room temperature. The product was filtered off and washed with cold methanol.

0.88 g of 8-methyl-5-(4-(N,N-dimethylsulfamoyl)phenyl)-6-7-8-9-tetrahydro-1H-pyrrolo[3,2-h]-isoquinoline-2,3-dione-3-O-(3-(2-oxo)tetrahydrofuryl)oxime, hydrochloride was obtained. M.p. 245° C. (decomposes).

The following compounds were prepared analogously:

8-methyl-5-(4-(N,N-dimethylsulfamoyl)phenyl)-6-7-8-9-tetrahydro-1H-pyrrolo[3,2h]-isoquinoline-2,3-dione-3-O-(5-(4-bromo-3-ethoxy)isoxazolylmethyl)oxime hydrochloride. M.p. 265° C. (decomposes);

8-methyl-5-(4-(N,N-dimethylsulfamoyl)phenyl)-6-7-8-9-tetrahydro-1H-pyrrolo[3,2h]-isoquinoline-2,3-dione-3-O-(4-(N,5-dimethyl-3-xo)isoxazolylmethyl)oxime hydrochloride. M.p. 260° C. (decomposes);

8-methyl-5-(4-(N,N-dimethylsulfamoyl)phenyl)-6-7-8-9-tetrahydro-1H-pyrrolo[3,2h]-isoquinoline-2,3-dione-3-O-(4-(N-methyl-5-tertbutyl-3-oxo)isoxazolylmethyl)oxime hydrochloride. M.p. 260° C. (decomposes); and 8-methyl-5-(4-(N,N-dimethylsulfamoyl)phenyl)-6-7-8-9-tetrahydro-1H-pyrrolo[3,2h]-isoquinoline-2,3-dione-3-O-(4-(5-methyl-3-ethoxy)isoxazolylmethyl)oxime hydrochloride.

Example 23

8-methyl-5-(4-(N,N-dimethylsulfamoyl)phenyl)-6-7-8-9-tetrahydro-1H-pyrrolo[3,2-h]-isoquinoline-2,3-dione-3-O-(3-(2-oxo)tetrahydrofuryl)oxime (0.6 g) was stirred at room temperature for 24 hours in water (5 ml) and 1N NaOH (aq) in such amounts that assured a pH around 12. The reaction mixture was extracted with ethylacetate. The aqueous layer was separated and reduced in vacuo to a volume of 2 ml. Addition of isopropanol (10–15 ml) afforded a yellow solid precipitate of the title compound.

8-methyl-5-(4-(N,N-dimethylsulfamoyl)phenyl)-6-7-8-9-tetrahydro-1H-pyrrolo[3,2-h]-isoquinoline-2,3-dione- 3-O-(4-hydroxybutyric acid-2-yl)oxime sodium salt, m.p.>200° C. (decomposes; dark at 190° C.).

Example 24

Biological Activity

In an in vitro activity (receptor affinity) test, the chemical compounds of the present invention have been tested for their affinity for the AMPA receptor.

L-glutamate (GLU) is the major excitatory neurotransmitter in the mammalian central nervous system. From electro-physiological- and binding studies, there appear to be at least three subtypes of GLU receptors, tentatively named N-methyl-D-aspartate (NMDA) receptors, quisqualate receptors and kainate receptors. AMPA has been known for several years to be a potent and selective agonist at the traditionally named quisqualate receptors. Activation of quisqualate receptors by AMPA is associated with $Na^+$ influx and $K^+$ efflux leading to depolarisation. $^3$H-AMPA is a selective radioligand for labelling the ionotropic quisqualate (AMPA) receptors.

Tissue preparation

Preparations are performed at 0–4° C. unless otherwise indicated. Cerebral cortex from male Wistar rats (150–200 g) is homogenised for 5–10 sec in 20 ml Tris-HCl (30 mM, pH 7.4) using an Ultra-Turrax™ homogeniser. The suspension is centrifuged at 27,000×g for 15 minutes and the pellet is washed three times with buffer (centrifuged at 27,000×g for 10 minutes). The washed pellet is homogenised in 20 ml of buffer and incubated on a water bath (of 37° C) for 30 minutes to remove endogenous glutamate and then centrifuged for 10 minutes at 27,000×g. The pellet is then homogenised in buffer and centrifuged at for 10 minutes at 27,000×g. The final pellet is resuspended in 30 ml buffer and the preparation is frozen and stored at −20° C.

Assay

The membrane preparation is thawed and centrifuged at 2° C. for 10 minutes at 27,000×g. The pellet is washed twice with 20 ml 30 mM Tris-HCl containing 2.5 mM $CaCl_2$, pH 7.4, using an Ultra-Turrax™ homogeniser and centrifuged for 10 minutes at 27,000×g. The final pellet is resuspended in 30 mM Tris-HCl containing 2.5 mM $CaCl_2$ and 100 mM KSCN, pH 7.4 (100 ml per g of original tissue) and used for binding assays. Aliquots of 0.5 (0.2) ml are added to 25 (20) μl of test solution and 25 (20) μl of $^3$H-AMPA (5 nM, final concentration), mixed and incubated for 30 minutes at 2° C. Non-specific binding is determined using L-glutamate (0.6 mM, final concentration).

After incubation the 550 μl samples are added 5 ml of ice-cold buffer and poured directly onto Whatman™ GF/C glass fibre filters under suction and immediately washed with 5 ml of ice-cold buffer. The 240 μl samples are filtered over glass fibre filter using a Skatron™ cell harvester. The filters are washed with 3 ml ice-cold buffer. The amount of radioactivity on the filters is determined by conventional liquid scintillation counting. Specific binding is total binding minus non-specific binding.

The test value is given as the $IC_{50}$ (the concentration (μM) of the test substance which inhibits the specific binding of $^3$H-AMPA by 50%).

From this test it was found that:

8-methyl-5-(4-(N,N-dimethylsulphamoyl)phenyl-6,7,8,9-tetrahydro-1H-pyrrolo[3,2-h]isoquinoline-2,3-dione-3-O-(ethoxycarbonylmethyl)oxime of the invention have an $IC_{50}$ value of 0.1 μM;

8-methyl-5-(4-(N,N-dimethylsulfamoyl)phenyl)-6-7-8-9-tetrahydro-1H-pyrrolo[3,2-h]-isoquinoline-2,3-dione- 3-O-(3-(2-oxo)tetrahydrofuryl)oxime of the invention have an $IC_{50}$ value of 0.15 μM; and 8-methyl-5-(4-(N,N-dimethylsulfamoyl)phenyl)-6-7-8-9-tetrahydro-1H-pyrrolo[3,2-h]isoquinoline-2,3-dione-3-O-(4-hydroxybutyric acid-2-yl)oxime of the invention have an $IC_{50}$ value of 0.05 μM.

What is claimed is:

1. A method of combating diseases and disorders associated with or mediated by the release of excitatory amino acids, said method comprising administering to a subject a compound of the general formula (I):

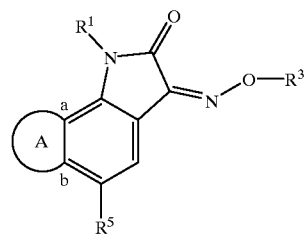

wherein $R^1$ represents hydrogen, alkyl or benzyl;

$R^3$ represents "Het", or a group of the following formula

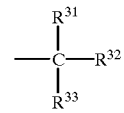

wherein

"Het" represents a saturated or unsaturated, 4 to 7 membered, monocyclic, heterocyclic ring, which ring may optionally be substituted one or more times with substituents selected from the group consisting of halogen, alkyl, alkoxy, and oxo; and at least one of $R^{31}$, $R^{32}$, and $R^{33}$ independently represents hydrogen, alkyl, or hydroxyalkyl, and at least one of $R^{31}$, $R^{32}$, and $R^{33}$ independently represents $(CH_2)_n R^{34}$;

wherein $R^{34}$ represents hydroxy, carboxy, alkoxycarbonyl, alkenyloxycarbonyl, alkynyloxycarbonyl, cycloalkoxycarbonyl, cycloalkyl-alkoxycarbonyl, aryloxycarbonyl, aralkoxycarbonyl, $CONR^{35}R^{36}$, or "Het"; wherein $R^{35}$ and $R^{36}$ represents hydrogen, alkyl, alkenyl, alkynyl, hydroxyalkyl, cycloalkyl, aryl, aralkyl, or $(CH_2)_n$—$R^{37}$; wherein $R^{37}$ represents hydroxy, carboxy, alkoxycarbonyl, alkenyloxycarbonyl, alkynyloxycarbonyl, cycloalkoxycarbonyl, cycloalkylalkoxycarbonyl, aryloxycarbonyl, or aralkoxycarbonyl; or $R^{35}$ and $R^{36}$ together with the N-atom to which they are attached form a saturated 5- to 6-membered, heterocyclic ring, optionally containing one additional N or O atom; and "Het" is as defined above; and n is 0, 1, 2, or 3; and $R^5$ represents phenyl, naphthyl, thienyl, or pyridyl, all of which may be substituted one or more times with substituents selected from the group consisting of halogen, $CF_3$, $NO_2$, amino, alkyl, alkoxy, phenyl and $SO_2NR^{51}R^{52}$;

wherein
$R^{51}$ and $R^{52}$ each independently represents hydrogen or alkyl; or $R^{51}$ and $R^{52}$ together with the N-atom to which they are attached form a saturated 4- to 7-membered, monocyclic, heterocyclic ring, optionally containing one additional N or O atom; and "A" represents a ring of five to seven atoms fused with the benzo ring at the positions marked "a" and "b", and formed by the following bivalent radicals:

a-$NR^6$—$CH_2$—$CH_2$-b;
a-$CH_2$—$NR^6$—$CH_2$-b;
a-$CH_2$—$CH_2$—$NR^6$-b;
a-$NR^6$—$CH_2$—$CH_2$—$CH_2$-b;
a-$CH_2$—$NR^6$—$CH_2$—$CH_2$-b;
a-$CH_2$—$CH_2$—$NR^6$—$CH_2$-b;
a-$CH_2$—$CH_2$—$CH_2$—$NR^6$-b;
a-$NR^6$—$CH_2$—$CH_2$—$CH_2$—$CH_2$-b;
a-$CH_2$—$NR^6$—$CH_2$—$CH_2$—$CH_2$-b;
a-$CH_2$—$CH_2$—$NR^6$—$CH_2$—$CH_2$-b;
a-$CH_2$—$CH_2$—$CH_2$—$NR^6$—$CH_2$-b; or
a-$CH_2$—$CH_2$—$CH_2$—$CH_2$—$NR^6$-b; wherein
$R^6$ represents hydrogen, alkyl or $CH_2CH_2OH$;
or a pharmaceutically acceptable salt thereof.

2. The method according to claim 1, wherein "Het" is a lactone ring of the general formula (VI):

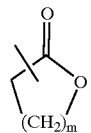

wherein m is 1, 2, 3 or 4.

3. The method according to either of claims 1–2, wherein the chemical compound is represented by the general formula (II):

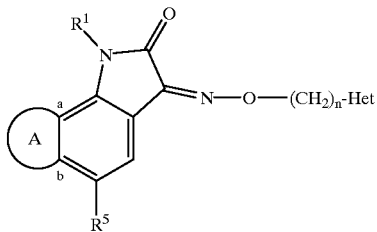

wherein
$R^1$ represents hydrogen, alkyl or benzyl;
"Het" represents a saturated or unsaturated, 4 to 7 membered, monocyclic, heterocyclic ring, which ring may optionally be substituted one or more times with substituents selected from the group consisting of halogen, alkyl, alkoxy, and oxo;
n is 0, 1, 2, or 3;
$R^5$ represents phenyl, naphthyl, thienyl, or pyridyl, all of which may be substituted one or more times with substituents selected from the group consisting of halogen, $CF_3$, $NO_2$, amino, alkyl, alkoxy, phenyl and $SO_2NR^{51}R^{52}$;

wherein
$R^{51}$ and $R^{52}$ each independently represents hydrogen or alkyl; or $R^{51}$ and $R^{52}$ together with the N-atom to which they are attached form a saturated 4- to 7-membered, monocyclic, heterocyclic ring, optionally containing one additional N or O atom; and "A" represents a ring of five to seven atoms fused with the benzo ring at the positions marked "a" and "b", and formed by the following bivalent radicals:

a-$NR^6$—$CH_2$—$CH_2$-b;
a-$CH_2$—$NR^6$—$CH_2$-b;
a-$CH_2$—$CH_2$—$NR^6$-b;
a-$NR^6$—$CH_2$—$CH_2$—$CH_2$-b;
a-$CH_2$—$NR^6$—$CH_2$—$CH_2$-b;
a-$CH_2$—$CH_2$—$NR^6$—$CH_2$-b;
a-$CH_2$—$CH_2$—$CH_2$—$NR^6$-b;
a-$NR^6$—$CH_2$—$CH_2$—$CH_2$—$CH_2$-b;
a-$CH_2$—$NR^6$—$CH_2$—$CH_2$—$CH_2$-b;
a-$CH_2$—$CH_2$—$NR^6$—$CH_2$—$CH_2$-b;
a-$CH_2$—$CH_2$—$CH_2$—$NR^6$—$CH_2$-b; or
a-$CH_2$—$CH_2$—$CH_2$—$CH_2$—$NR^6$-b; wherein
$R^6$ represents hydrogen, alkyl or $CH_2CH_2OH$.

4. The method according to claim 3, wherein
n is 0, 1 or 2; and
$R^5$ represents phenyl or pyridyl, both of which may be substituted one or more times with substituents selected from the group consisting of halogen, $CF_3$, $NO_2$, amino, alkyl, alkoxy, phenyl and $SO_2NR^{51}R^{52}$;

wherein
$R^{51}$ and $R^{52}$ each independently represents hydrogen or alkyl; or $R^{51}$ and $R^{52}$ together with the N-atom to which they are attached form a chain —$(CH_2)_m$—,
wherein m is 2, 3, 4, 5 or 6.

5. The method according to claim 3, wherein the chemical compound is represented by the general formula (III):

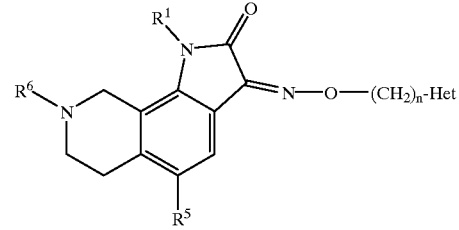

wherein
$R^1$, $R^5$, $R^6$, "Het", and n are as defined in claim 3.

6. The method according to claim 1, wherein "Het" is a lactone of the general formula (VII):

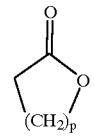

wherein p is 1, 2, 3, or 4.

7. The method according to claim 3, wherein the chemical compound is
8-methyl-5-(4-(N,N-dimethylsulfamoyl)phenyl)-6-7-8-9-tetrahydro-1H-pyrrolo[3,2-h]-isoquinoline-2,3-dione-3-O-(3-(2-oxo)tetrahydrofuryl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(5-(4-bromo-3-methoxy)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(5-(4-bromo-3-ethoxy)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(4-(N,5-dimethyl-3-oxo)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(4-(N-methyl-5-tertbutyl-3-oxo)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(4-(5-methyl-3-methoxy)isoxazolylmethyl)oxime; or 8-methyl-5-(4-(N,N-dimethylsulfamoyl)phenyl)-6-7-8-9-tetrahydro-1H-pyrrolo[3,2h]-isoquinoline-2,3-dione-3-O-(4-(5-methyl-3-ethoxy)isoxazolylmethyl)oxime;

or a pharmaceutically acceptable salt hereof.

8. The method according to claim 1, wherein the chemical compound is represented by the general formula (IV):

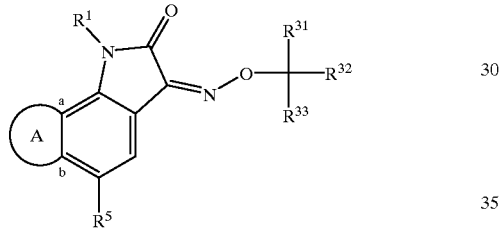

wherein $R^1$ represents hydrogen, alkyl or benzyl; at least one of $R^{31}$, $R^{32}$, and $R^{33}$ independently represents hydrogen, alkyl, or hydroxyalkyl, and at least one of $R^{31}$, $R^{32}$, and $R^{33}$ independently represents $(CH_2)_n R^{34}$; wherein $R^{34}$ represents hydroxy, carboxy, alkoxycarbonyl, alkenyloxycarbonyl, alkynyloxycarbonyl, cycloalkoxycarbonyl, cycloalkyl-alkoxycarbonyl, aryloxycarbonyl, aralkoxycarbonyl, or $CONR^{35}R^{36}$; wherein $R^{35}$ and $R^{36}$ represents hydrogen, alkyl, alkenyl, alkynyl, hydroxyalkyl, cycloalkyl, aryl, aralkyl, or $(CH_2)_n—R^{37}$; wherein $R^{37}$ represents hydroxy, carboxy, alkoxycarbonyl, alkenyloxycarbonyl, alkynyloxycarbonyl, cycloalkoxycarbonyl, cycloalkyl-alkoxycarbonyl, aryloxycarbonyl, or aralkoxycarbonyl; or $R^{35}$ and $R^{36}$ together with the N-atom to which they are attached form a saturated 5- to 6-membered, heterocyclic ring, optionally containing one additional N or O atom; and n is 0, 1, 2, or 3; or one of $R^{31}$, $R^{32}$, and $R^{33}$ represents hydrogen or alkyl, and two of $R^{31}$, $R^{32}$, and $R^{33}$ together form a lactone ring of the general formula (VI):

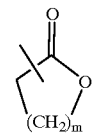

wherein m is 1, 2 or 3; and $R^5$ represents phenyl, naphthyl, thienyl, or pyridyl, all of which may be substituted one or more times with substituents selected from the group consisting of halogen, $CF_3$, $NO_2$, amino, alkyl, alkoxy, phenyl and $SO_2NR^{51}R^{52}$;

wherein $R^{51}$ and $R^{52}$ each independently represents hydrogen or alkyl; or $R^{51}$ and $R^{52}$ together with the N-atom to which they are attached form a saturated 4- to 7-membered, monocyclic, heterocyclic ring, optionally containing one additional N or O atom; and "A" represents a ring of five to seven atoms fused with the benzo ring at the positions marked "a" and "b", and formed by the following bivalent radicals:

a-$NR^6$—$CH_2$—$CH_2$-b;
a-$CH_2$—$NR^6$—$CH_2$-b;
a-$CH_2$—$CH_2$—$NR^6$-b;
a-$NR^6$—$CH_2$—$CH_2$—$CH_2$-b;
a-$CH_2$—$NR^6$—$CH_2$—$CH_2$-b;
a-$CH_2$—$CH_2$—$NR^6$—$CH_2$-b;
a-$CH_2$—$CH_2$—$CH_2$—$NR^6$-b;
a-$NR^6$—$CH_2$—$CH_2$—$CH_2$—$CH_2$-b;
a-$CH_2$—$NR^6$—$CH_2$—$CH_2$—$CH_2$-b;
a-$CH_2$—$CH_2$—$NR^6$—$CH_2$—$CH_2$-b;
a-$CH_2$—$CH_2$—$CH_2$—$NR^6$—$CH_2$-b; or
a-$CH_2$—$CH_2$—$CH_2$—$CH_2$—$NR^6$-b; wherein $R^6$ represents hydrogen, alkyl or $CH_2CH_2OH$;

or a pharmaceutically acceptable salt thereof.

9. The method according to claim 8, wherein the chemical compound is represented by the general formula (V):

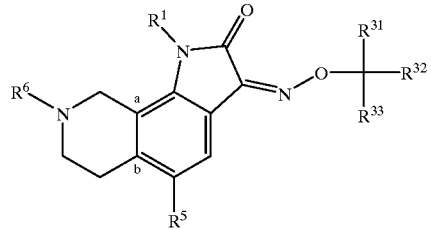

wherein $R^1$, $R^{31}$, $R^{32}$, $R^{33}$, $R^5$, and $R^6$ are as defined in claim 8.

10. The method according to claim 8, wherein the chemical compound is 1-methyl-8-methyl-5-phenyl-6,7,8,9-tetrahydro-pyrrolo[3,2-h]isoquinoline-2,3-dione-3-O-(carboxymethyl)oxime;

1-methyl-8-methyl-5-phenyl-6,7,8,9-tetrahydro-1H-pyrrolo[3,2h]-isoquinoline-2,3-dione-3-O-(ethoxycarbonylmethyl)oxime;

1-methyl-8-methyl-5-(4-(N,N-dimethylsulfamoyl)phenyl)-6,7,8,9-tetrahydro-pyrrolo[3,2-h]isoquinoline-2,3-dione-3-O-(carboxymethyl)oxime;

1-methyl-8-methyl-5-(4-(N,N-dimethylsulfamoyl)phenyl)-6,7,8,9-tetrahydro-1H-pyrrolo[3,2-h]

isoquinoline-2,3-dione-3-O-(1-ethoxycarbonyl-1-methylethyl)oxime;

1-methyl-8-methyl-5-(4-(N,N-dimethylsulfamoyl)phenyl-6,7,8,9-tetrahydro-pyrrolo[3,2-h]isoquinoline-2,3-dione-3-O-(ethoxycarbonylmethyl)oxime;

8-methyl-5-phenyl-6,7,8,9-tetrahydro-1H-pyrrolo[3,2-h]-isoquinoline-2,3-dione-3-O-(carboxymethyl)oxime;

8-methyl-5-phenyl-6,7,8,9-tetrahydro-1H-pyrrolo[3,2-h]isoquinoline-2,3-dione-3-O-(1-carboxy-1-methylethyl)oxime;

8-methyl-5-phenyl-6,7,8,9-tetrahydro-1H-pyrrolo[3,2-h]isoquinoline-2,3-dione-3-O-(ethoxycarbonylmethyl)oxime;

8-methyl-5-phenyl-6,7,8,9-tetrahydro-1H-pyrrolo[3,2-h]isoquinoline-2,3-dione-3-O-(isopropoxycarbonylmethyl)oxime;

8-methyl-5-phenyl-6,7,8,9-tetrahydro-1H-pyrrolo[3,2-h]isoquinoline-2,3-dione-3-O-(1-ethoxycarbonyl-1-methyl)ethyloxime;

8-methyl-5-phenyl-6,7,8,9-tetrahydro-1H-pyrrolo[3,2-h]isoquinoline-2,3-dione-3-O-(t-butoxycarbonylmethyl)oxime;

8-methyl-5-phenyl-6,7,8,9-tetrahydro-1H-pyrrolo[3,2-h]isoquinoline-2,3-dione-3-O-(N,N-dimethylcarbamoylmethyl)oxime;

8-methyl-5-phenyl-6,7,8,9-tetrahydro-1H-pyrrolo[3,2-h]isoquinoline-2,3-dione-3-O-(N-methylcarbamoylmethyl)oxime;

8-methyl-5-phenyl-6,7,8,9-tetrahydro-1H-pyrrolo[3,2-h]isoquinoline-2,3-dione-3-O-(N-phenylcarbamoylmethyl)oxime;

8-methyl-5-phenyl-6,7,8,9-tetrahydro-1H-pyrrolo[3,2-h]isoquinoline-2,3-dione-3-O-(N,N-di(2-hydroxyethyl)carbamoylmethyl)oxime;

8-methyl-5-phenyl-6,7,8,9-tetrahydro-1H-pyrrolo[3,2-h]isoquinoline-2,3-dione-3-O-(morpholinocarbonylmethyl)oxime;

8-methyl-5-phenyl-6,7,8,9-tetrahydro-1H-pyrrolo[3,2-h]isoquinoline-2,3-dione-3-O-(ethoxycarbonylmethylcarbamoylmethyl)oxime;

8-methyl-5-phenyl-6,7,8,9-tetrahydro-1H-pyrrolo[3,2-h]isoquinoline-2,3-dione-3-O-(N,N-di(2-(N,N-diethylamino)ethyl)carbamoyl)oxime;

8-methyl-5-(4-(N,N-dimethylsulfamoyl)phenyl)-6,7,8,9-tetrahydro-1H-pyrrolo[3,2-h]-isoquinoline-2,3-dione-3-O-(carboxymethyl)oxime;

8-methyl-5-(4-(N,N-dimethylsulfamoyl)phenyl)-6,7,8,9-tetrahydro-1H-pyrrolo[3,2-h]isoquinoline-2,3-dione-3-O-(2-hydroxyethyl)oxime;

8-methyl-5-(4-(N,N-dimethylsulfamoyl)phenyl)-6,7,8,9-tetrahydro-1H-pyrrolo[3,2-h]isoquinoline-2,3-dione-3-O-(1-carboxy-1-methylethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(ethoxycarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(cyclopropylmethoxycarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(isopropoxycarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(N,N-dimethylcarbamoylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(piperidinocarbonylmethyl)oxime;

8-methyl-5-(4-(piperidinosulfonyl)phenyl-6,7,8,9-tetrahydro-1H-pyrrolo[3,2-h]isoquinoline-2,3-dione-3-O-(piperidinocarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(morpholinocarbonylmethyl)oxime; or 8-methyl-5-(4-(N,N-dimethylsulfamoyl)phenyl)-6-7-8-9-tetrahydro-1H-pyrrolo[3,2-h]isoquinoline-2,3-dione-3-O-(4-hydroxybutyric acid-2-yl)oxime;

or a pharmaceutically acceptable salt hereof.

* * * * *